United States Patent [19]

Jensen

[11] 4,198,714

[45] Apr. 22, 1980

[54] INTRAOCULAR LENS FOR IMPLANTATION INTO THE POSTERIOR CHAMBER OF A HUMAN EYE

[76] Inventor: Ronald P. Jensen, 4156 Dorset Pl., Flintridge, Calif. 91103

[21] Appl. No.: 938,225

[22] Filed: Aug. 30, 1978

Related U.S. Application Data

[63] Continuation-in-part of Ser. No. 794,467, May 6, 1977, Pat. No. 4,110,848.

[51] Int. Cl.² .................... A61F 1/16; A61F 1/24
[52] U.S. Cl. ........................................... 3/13
[58] Field of Search .............. 3/13; 351/163, 165, 351/167; 350/1.6

[56] References Cited

U.S. PATENT DOCUMENTS

| Re. 27473 | 9/1972 | Mauer | 351/44 X |
|---|---|---|---|
| 3,034,403 | 5/1962 | Neefe | 3/13 X |
| 3,906,551 | 9/1975 | Otter | 3/13 |
| 3,925,825 | 12/1975 | Richards et al. | 3/13 |
| 3,994,027 | 11/1976 | Jensen et al. | 3/13 |

FOREIGN PATENT DOCUMENTS

730640 5/1955 United Kingdom ............ 3/13
810232 3/1959 United Kingdom ............ 3/13

Primary Examiner—Ronald L. Frinks
Attorney, Agent, or Firm—W. Edward Johansen

[57] ABSTRACT

The present invention is an intraocular lens for implantation into the posterior chamber of a human eye. The intraocular lens includes a plano-convex lens which is formed from an optical material that is suitable for an implanatable lens. The plano-convex lens is adapted to be inserted into the posterior chamber of the human eye within the capsular membrane thereof. The intraocular lens also includes a first supporting loop and a second supporting loop, which are formed from a material that is suitable for implantation into the eye, mechanically coupled to the peripheral edge of plano-convex lens and disposed at an angle in the range of 0° to 25° to the plane surface of the plano-convex lens so that their end portions are below the plane surface of the plano-convex lens. The second supporting loop has a third loop which is formed from supramid material and which is mechanically coupled thereto between the peripheral edge of the plano-convex lens and its end portion so that a temporary securement to the iris of the human eye may be accomplished.

5 Claims, 4 Drawing Figures

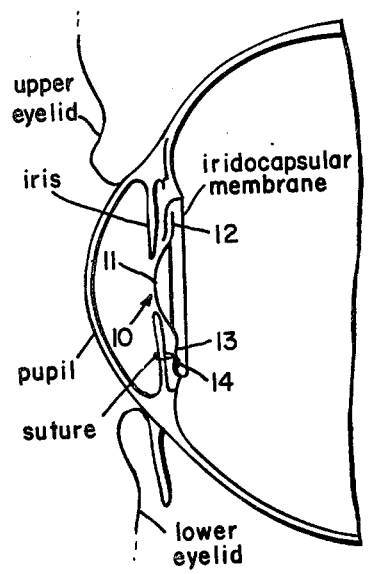
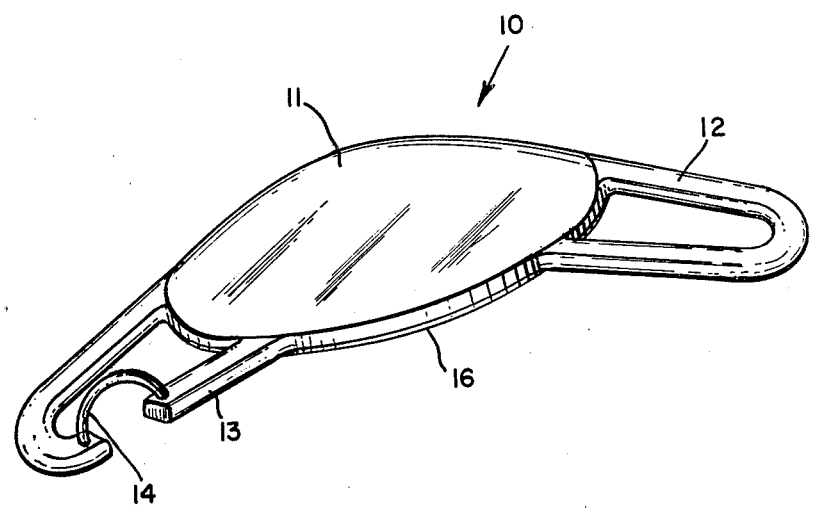
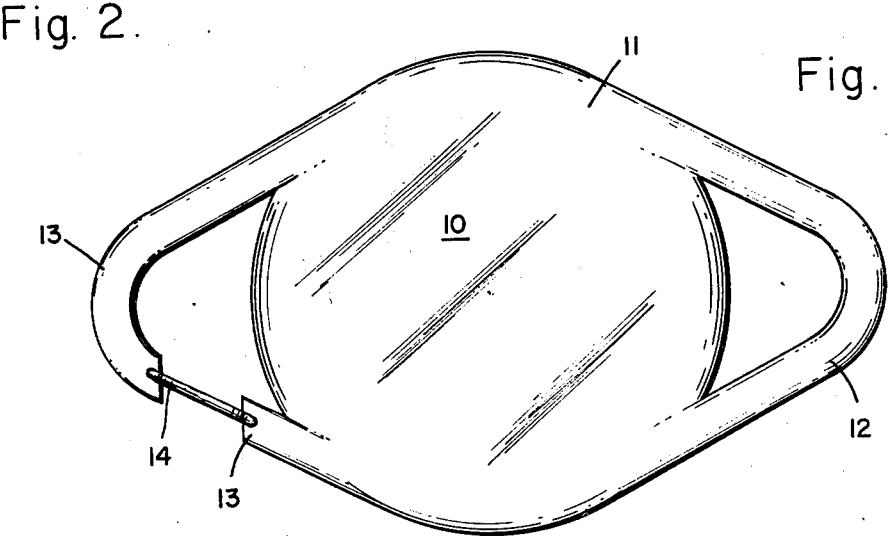
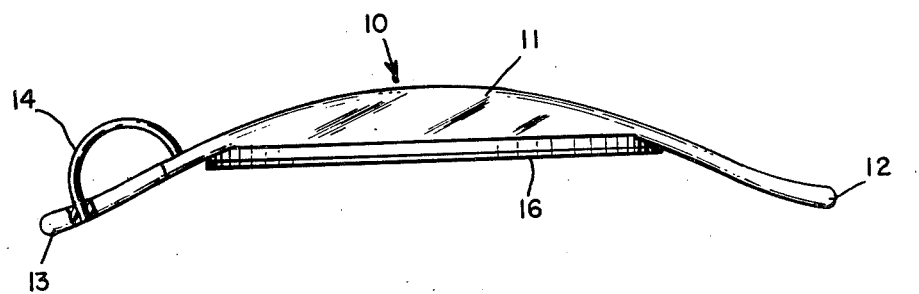

INTRAOCULAR LENS FOR IMPLANTATION INTO THE POSTERIOR CHAMBER OF A HUMAN EYE

The application is a continuation-in-part of an application, entitled An Intraocular Lens for Implantation into the Posterior Chamber of a Human Eye, filed by Ronald P. Jensen on May 6, 1977 and having Ser. No. 794,467, now U. S. Pat. No. 4,110,848, issued Sept. 5, 1978.

BACKGROUND OF THE INVENTION

1. Field of the Invention

The present invention relates to an improved prepupillary lens which may be surgically implanted into the posterior chamber of a human eye and more particularly to a method for securing the lens within the chamber.

2. Description of the Prior Art

In the prior art prepupillary lenses have been used in an operation for surgically implanting a lens on the iris of a human eye. Cornelius D. Binkhorst, M.D., who has performed this operation since 1958, has used a two loop lens and a four-loop lens. He has described both of these lenses in an article entitled "The Iridocapsular (Two-loop) Lens and the Iris-clip (Four-loop) Lens in Pseudophakia", which he wrote for the 1973 September–October edition of Transactions of the American Academy of Opthalmology and Otolaryngology. These lenses are made from a plastic material, polymethyl methacrylate, which is commonly used to make contact lenses. The lenses are in the shape of a plano convex lens and have a diameter of 5.0 millimeters and a central thickness of from 0.5 millimeters to 0.6 millimeters depending on the required lens strength.

U.S. Pat. No. 3,994,027, entitled Prepupillary Lens for Implanting in a Human Eye, issued to Ronald P. Jensen and James Fetz on Nov. 30, 1976 teaches a two-loop lens which has its loops buried in the posterior chamber of the human eye, but which rests within the anterior chamber of the human eye. The difficulty with this position of the two-loop lens is that this is not the normal position of the original lens. The placement of the lens in the anterior chamber of the human eye is unnatural and creates a problem in the restoration of accurate binocular vision. Further the lens in the anterior chamber is not adjacent to the hyloid membrane for supporting the vitreous humor thereby making instances of forward displacement of the vitreous humor and retinal detachment more likely to occur.

Another difficulty with this type of lens is that it is formed out of a plastic material which transmits infrared light and ultraviolet light to the retina.

The prior art also teaches an artificial intraocular lens for implantation in the posterior chamber of an eye which includes an optical zone portion fabricated of transparent material and shaped similar to a natural lens and a plurality of prongs attached to the optical zone portion near its periphery. The prongs protrude forwardly therefrom for insertion through the iris of the eye to hold and position the lens therein. The difficulty with this lens is that it is affixed to the iris of the eye and therefore it is not rigidly anchored thereby allowing the lens to move with eye movement. Subsequently, the iris may erode and the fixation of the lens may be lost. It would be far better to anchor the intraocular lens within the posterior chamber to the capsular membrane which is a very firm, non-viable tissue and which provides firm, secure and permanent fixation of the lens.

Another prior art device teaches a lens for implantation in the eye which has a resilient flange that is sutured to the ciliary muscle of the eye to position and to retain the lens in the same position as the original lens. This lens irritates the ciliary body so that inflammation is likely to occur. The fixation of the lens to the ciliary body is not only a difficult surgical procedure, but also does not provide a firm, secure or permanent fixation of the lens.

U.S. Pat. No. 3,913,148, entitled Intraocular Lens Apparatus, issued to Ernst W. Potthast on Oct. 21, 1975, U.S. Pat. No. 3,991,426, entitled Posterior Chamber Artificial Intraocular Lens with Retaining Means and Instruments for Use Therewith, issued to Leonard Flom and Kenneth J. Rodgerson Nov. 16, 1976, and U.S. Pat. No. 4,014,049, entitled Artificial Intraocular Lens and Supporting System Therefor, all teach intraocular lenses that are positioned in the posterior chamber of the eye and that are fixated to the iris of the eye.

U.S. Pat. No. 4,079,470, entitled Artificial Intraocular Lens, issued to Emil W. Deeg and David A. La Marre on Mar. 2, 1978, teaches a chemically durable biologically inert optical implant lens formed of a low density natural or synthetic crystal, such as Corundum, Sapphire, Ruby, Sircon, Strontium, Diamond or Anatase. Special sprectral transmittances desired for specific color vision effects and ultraviolet protection may be accomplished by synthetic crystals. These metal ions absorb the ultraviolet rays within the intraocular lens.

The inventor refers to an application having Ser. No. 862,534, filed on Dec. 20, 1977 by Michael E. Fourney and Ronald P. Jensen, entitled An Infra-red Reflective Coating for Protecting Eye of Cataract Patients (now abandoned), and hereby incorporates the material by reference thereto.

Another prior art intraocular lens teaches a chemically durable, inert optical implant lens formed out of a glass composition which has spectral transmission characteristics simulating those of human crystalline lenses and which specifically absorbs ultraviolet light. This implant lens is too heavy for a human eye, because it is basically formed out of glass and has a density in the range of 2.46 to 3.05 grams per cubic centimeters. The plastic lenses have a density of approximately 1.0 grams per cubic centimeters. It is therefore desirable to obtain the advantage of both the low density of the plastic lenses and the infrared transmission characteristic of this particular glass lens.

The inventor has studied the various methods of making implant lenses and has come to the conclusion that it is better to reflect the infrared radiation and the ultraviolet radiation than it is to absorb them because those lenses which absorb the infrared radiation and ultraviolet radiation have a tendency to lower the transmission of the visible radiation in the absorption process.

SUMMARY OF THE INVENTION

In view of the foregoing factors and conditions of the prior art it is a primary object of the present invention to provide an intraocular that is positioned in the posterior chamber and is anchored securely in the capsular membrane formed by the anterior and posterior capsules adhering together.

It is another object of the present invention to provide an intraocular lens that requires only one, temporary securement to the iris of the eye until capsular fixation occurs.

It is still another object of the present invention to provide a prepupillary lens that is not only of the same density as the lens of a human eye, but also reflects radiation of the ultraviolet spectrum and the infrared spectrum while transmitting radiation of the visible spectrum.

It is yet another object of the present invention to provide an intraocular lens for implantation into the capsular membrane that does not have a supporting member which protrudes above the iris so that in the future glaucoma surgery may be performed and additionally so that the iris is free to move in a normal manner.

It is still yet another object of the present invention to provide an intraocular lens for implantation in the posterior chamber which will eliminate edge reflection which occurs in the lenses implanted in the anterior chamber and which will minimize internal reflection by eliminating the posts required by the other posterior lenses.

It is yet still another object of the present invention to provide an intraocular lens for implantation in the posterior chamber that is not only a strong and secure fixation, but also a lifetime fixation.

In accordance with an embodiment of the present invention an intraocular lens for implantation into the posterior chamber of a human eye is described. The intraocular lens includes a plano-convex lens, which is formed from an optical material that is suitable for an implantable lens. The plano-convex is adapted to be inserted into the posterior chamber of the human eye within the capsular membrane thereof. The intraocular lens also includes a first supporting loop and a second supporting loop, which are formed from the material that is suitable for implantation into the eye, mechanically coupled to the peripheral edge of the plano-convex lens and disposed at an angle in the range of 0° to 25° to the plane surface of the plano-convex lens so that their end portions are below the plane surface of planoconvex lens. The second supporting loop has a third loop which is formed from supramid(polymercaptan) material and which is mechanically coupled thereto between the peripheral edge of the plano-convex lens and its end portion so that a temporary securement to the iris of the human eye may be accomplished. In the preferred embodiemnt of the present invention the plano-convex lens and the first and second supporting loops are molded into one integral member.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figure.

DESCRIPTION OF THE DRAWING

FIG. 1 is a perspective drawing of an intraocular lens which has been constructed in accordance with the principles of the present invention.

FIG. 2 is a shcematic drawing of a human eye in which the intraocular lens of FIG. 1 has been implanted within the posterior chamber thereof.

FIG. 3 is a plan view of the intraocular lens of FIG. 1.

FIG. 4 is a side elevational view of intraocular lens of FIG. 1.

DESCRIPTION OF THE PREFERRED EMBODIMENT

In order to best understand the present invention a description of the preferred embodiment thereof is provided accompanied by a drawing. In FIG. 1 a perspective view of an intraocular lens 10 for implantation in the posterior chamber of a human eye is shown. The intraocular lens 10 has a plano-convex lens, which is formed from an optical material that is suitable for an implantable lens, which is adapted to be inserted into the posterior chamber of the human eye within the capsular membrane thereof. The optical material most commonly used is polymethyl methacrylate. The intraocular lens 10 also has a first supporting loop 12, which is formed from a material that is suitable for implantation into the eye, mechanically coupled to the peripheral edge of the plano-convex lens 11 and disposed at an angle in the range of 0° to 25° to the plane surface of the plano-convex lens 11 so that its end portion is below the surface thereof. The intraocular lens 10 further has a second supporting loop 13, which is also formed from a material that is suitable for implantation into the eye, mechanically coupled to the peripheral edge of the plano-convex lens 11 and disposed at an angle in the range of 0° to 25° to the plane surface of the plano-convex lens 11 so that its end portion is below the surface thereof. The second supporting loop 13 has a third loop 14 which is formed from a flexible material and which is mechanically coupled thereto between its end portion and the peripheral edge of the plano-convex lens 11.

In the preferred embodiment the first and second supporting loops 12 and 13 are formed from the same material that the plano-convex lens 11 is formed from and combine with the plano-convex lens 11 to form an integral, molded intraocular lens 10.

Other embodiments of the intraocular lens 10 may be made by substituting metal wire or supramid(polymercaptan) wire and by attaching the wire to the planoconvex lens 11 by the methods taught in U.S. Pat. No. 3,994,027, which has been mentioned in the Description of the Prior Art.

Referring now to FIG. 2 a schematic drawing of the intraocular lens 10 shows it after it has been implanted into the capsular membrane of a human eye. One should note that a portion of the capsular membrane has been removed so that the intraocular lens 10 may be inserted behind the iris. The first supporting loop 12 is placed in a pocket of the remaining portion of the capsular membrane. The anterior side of this pocket and the posterior side of this pocket eventually scar together thereby securing the intraocular within the posterior chamber.

The inventor has inserted this lens 10 through the iris of a human eye into the capsular membrane so that the first supporting loop 12 slides into the pocket of the capsular membrane. He has then pulled the iris around the second supporting loop 13 so that the entire intraocular lens 10 could placed into the posterior chamber of the human eye. He has then sutured the third loop 14 of the second supporting loop 13 to the iris in order to provide a temporary securement to the iris for the intraocular lens 10. Once the posterior side and the anterior side of the pocket of the capsular membrane have scarred together there is no further need for suture coupling the third loop 14 to the iris because the intraocular lens 10 is firmly, permanently and securely fixated to the capsular membrane. Furthermore the iris is free to function normally. The third loop 14 may be sutured to the capsular membrane.

The use of the integral, molded member eliminates edge reflections which occur in lenses implanted in the anterior chamber and internal reflections which are caused by the posts for the supporting loops in other lenses implanted in the posterior chamber. Finally the use of this posterior intraocular lens 10 allows the patient to have glaucoma surgery in the future.

Referring now to FIG. 3 and FIG. 4 the intraocular lens 10 is shown in a plan view and a side elevational view. The purpose of hollow portion inside the first and second supporting loops 12 and 13 is not only to allow the implant surgeon to insert his implant tool beneath the lens 10 in order to support the lens 10 during its insertion into the capsular membrane, but also to facilitate the scarring of the posterior side and the anterior side of the pocket of the capsular membrane. The position of the third loop 14 in the second supporting loop 13 should not be above the plano-convex lens 11, but it should be adjacent to or above the plane surface of the plano-convex lens 11.

Referring to FIG. 4 the present invention also includes a plurality of layers 16 of dielectric material which are disposed on the planar surface of the lens 10. The plurality of layers 16 are adapted to form a dielectric stack for reflecting radiation of a particular spectral wavelength. The plurality of layers 16 may also be disposed on the convex surface of the lens 10.

From the foregoing it can be seen that an integral, molded intraocular lens for implantation into the posterior chamber of the human eye has been provided. It should be noted that the sketches are not drawn to scale and that thicknesses and distances of and between figures are not to be considered significant.

From the foregoing it can also be seen that a multilayer interference reflecting coating has been described for use in combination with a prepupillary lens to selectively reflect undesired radiation in the ultraviolet and infrared spectrums and to transmit visible light. The advantage of the dielectric stack is that it transmits close to one hundred percent of the visible light while reflecting virtually all of the undesired light. The dielectric stack is therefore not only effective as infrared reflector, but it also is effective in transmitting visible light so that the iris need not be more open than necessary for the amount of ambient light present.

Accordingly it is intended that the foregoing disclosure and showing made in the drawing shall be considered only an illustration of the principles of the present invention. The invention will be set out with particularity in the appended claims.

What is claimed is:

1. An intraocular lens for implantation in the posterior chamber of a human eye, said intraocular lens comprising:
   a. a plano-convex lens, which is formed from an optical material that is suitable for an implantable lens, which is adapted to be inserted into the posterior chamber of the human eye within the capsular membrane thereof;
   b. a first supporting loop, which is formed from a material that is suitable for implantation into the human eye, mechanically coupled to the peripheral edge of said plano-convex lens and disposed at an angle in the range of 0° to 25° to the plane surface of said plano-convex lens so that its end portion is below the plane surface of said plano-convex lens, said first supporting loop being adapted to secure said plano-convex lens rigidly and permanently in the posterior chamber of the human eye; and
   c. a second supporting loop, which is formed from a material that is suitable for implantation into the eye, mechanically coupled to the peripheral edge of said plano-convex lens and oppositely disposed to said first supporting loop, said second supporting loop being also disposed at an angle in the range of 0° to 25° to the plane surface of said plano-convex lens so that its end portion is below the plane surface of said plano-convex lens and having a third loop which is formed from a flexible material and which is mechanically coupled thereto between its end portion and the peripheral edge of said plano-convex lens so that a temporary securement to the iris of the human eye may be accomplished, said second supporting loop being also adapted to secure said plano-convex lens rigidly and permanently in the posterior chamber of the human eye.

2. An intraocular lens for implantation in the posterior chamber of a human eye according to claim 1 wherein said intraocular lens is an integral, molded member.

3. An intraocular lens for implantation in the posterior chamber of the human eye according to claim 2 wherein a gap in said second supporting loop is formed below the arc of said third loop in order so that the eye surgeon can more easily slip his needle under said third loop without being hindered by said second supporting loop.

4. An intraocular lens for implantation in the posterior chamber of a human eye according to claim 1 wherein said first and second supporting loops are formed from polymercaptan wire.

5. An intraocular lens for implantation in the posterior chamber of a human eye according to claim 1 wherein said first and second supporting loops are formed from metal wire.

* * * * *